United States Patent [19]

Holst et al.

[11] 4,068,068

[45] * Jan. 10, 1978

[54] PROCESS FOR THE MANUFACTURE OF WATER-ABSORBING CELLULOSE ETHERS

[75] Inventors: Arno Holst; Helmut Lask; Michael Kostrzewa, all of Weisbaden, Germany

[73] Assignee: Hoechst Aktiengesellschaft, Germany

[*] Notice: The portion of the term of this patent subsequent to Feb. 3, 1993, has been disclaimed.

[21] Appl. No.: 682,326

[22] Filed: May 3, 1976

[30] Foreign Application Priority Data

May 5, 1975 Germany .............................. 2519927

[51] Int. Cl.$^2$ ...................... C08B 11/00; C08B 11/20; C08B 15/10
[52] U.S. Cl. ................................... 536/88; 260/17 A; 536/87; 536/89; 536/98
[58] Field of Search ....................... 536/87, 88, 89, 98

[56] References Cited

U.S. PATENT DOCUMENTS

| 3,077,468 | 2/1963 | Geurden .............................. 536/87 |
| 3,272,640 | 9/1966 | Geurden .............................. 536/87 |
| 3,589,364 | 6/1971 | Dean et al. ........................ 128/284 |
| 3,723,413 | 3/1973 | Chatterjee et al. ................ 536/87 |
| 3,936,441 | 2/1976 | Holst et al. ......................... 536/98 |

Primary Examiner—Ronald W. Griffin
Attorney, Agent, or Firm—James E. Bryan

[57] ABSTRACT

This invention relates to an improvement in the process for the manufacture of water-adsorbing but at least partially water-insoluble cellulose ethers in which cellulose is alkalized in a liquid reaction medium and reacted with an etherification agent in a manner such that an at least preponderantly water-soluble cellulose ether would be obtained in the case of a mere etherification process and in which, prior to, simultaneously with, or after the etherification process, a reaction is effected with a crosslinking agent which is polyfunctional towards cellulose in an alkaline reaction medium, the improvement comprising employing bis(a-crylamido)-acetic acid as the crosslinking agent.

4 Claims, No Drawings

PROCESS FOR THE MANUFACTURE OF WATER-ABSORBING CELLULOSE ETHERS

The present invention relates to a process for the manufacture of water-adsorbing, but at least partially water-insoluble cellulose ethers.

It is known, for example from U.S. Pat. No. 3,589,364, that inherently water-soluble carboxymethyl cellulose obtained by etherification of cellulose with monochloroacetic acid may be crosslinked to produce a cellulose ether which is at least partially insoluble in water, but is capable of adsorbing relatively large quantities of water and of simultaneously swelling. Crosslinking may take place prior to, simultaneously with, or after etherification. Compounds which are polyfunctional towards cellulose are used as crosslinking agents, for example epoxy compounds, polychlorinated higher alcohols, or divinyl sulfone. Epichlorohydrin is preferred because in this case crosslinking may be effected simultaneously with etherificaton. The etherification processes take place either in the presence of water, in a semi-dry environment, or in the presence of relatively large quantities of an inert organic diluent, for example in the presence of isopropanol in a quantity amounting to 40 times the quantity of the cellulose. At room temperature, the crosslinking reaction requires many hours, for example 18 hours; at elevated temperature, the reaction proceeds more rapidly, but still requires several hours at a temperature of 70° C, for example 3.5 hours.

It is the object of the present invention to provide a quicker process for the manufacture of cellulose ethers which adsorb water, but are at least partially, i.e. by more than 20 per cent, insoluble in water. This object is achieved by proceeding from a known process for the manufacture of water-adsorbing, but substantially water-insoluble cellulose ethers in which cellulose is reacted with an etherification agent in the presence of an alkali in such a manner that a substantially, i.e. to at least 95 per cent by weight, water-soluble cellulose ether would be obtained in the case of a mere etherification process and in which prior to, simultaneously with, or after the etherification process, a reaction with a crosslinking agent is performed, which agent is polyfunctional towards cellulose in an alkaline reaction medium. The object of the present invention is achieved by using bis(acrylamido)-acetic acid as the crosslinking agent.

The process according to the present invention utilizes known etherification processes in which alkali cellulose is etherified in a manner such that a cellulose ether is produced which is at least substantially soluble in water. For practical reasons, the alkali cellulose used is almost invariably an alkali cellulose obtained by means of an aqueous NaOH solution, but etherification processes also may be conducted with alkali celluloses produced with aqueous KOH or LiOH solutions. Suitable etherification agents which may be used for the preparation of water-soluble cellulose ethers are, above all: sodium monochloroacetate, monochloroacetic acid, methyl chloride, ethylene oxide, and propylene oxide, either individually or in admixture with each other; ethyl chloride may also be used, especially in admixture with ethylene oxide or propylene oxide.

In addition to the etherification process, a crosslinking process is performed according to the process of the invention. The crosslinking reacction is conducted in a manner such that at least 20 per cent by weight of the resulting cellulose ether is no longer soluble in water, although the product is capable of swelling in water. The performance of such an additional crosslinking reaction is also known. What is novel in the present process is that bis(acrylamido)-acetic acid is used as the crosslinking agent, the chemical composition of this compound being identified by the formula $(CH_2 = CH - CO - NH)_2 : CHCOOH$. Preferably, 0.001 to 0.20 part by weight per part by weight of cellulose is applied.

If it is desired to produce a crosslinked cellulose ether having a very high water retention value (WRV), an organic solvent which is not reactive, or only slightly reactive, towards the reactants, e.g. dioxane, methyl ethyl ketone, ethanol, acetone, isopropanol, or tert. butyl alcohol, is used as the liquid reaction medium. Isopropanol is used with particular success. It is advisable to use 0.8 to 7.5 parts by weight of isopropanol per part by weight of the cellulose present as alkali cellulose. This statement refers to parts by weight calculated as 100 per cent isopropanol. In many cases, however, it is preferred to use isopropyl alcohol in the form of the hydrous product containing about 13 per cent by weight of water, which is frequently used for technical purposes. Further, in most cases aqueous alkali hydroxide solutions are used in order to provide the alkali necessary for the process. Thus, in addition to the water present when aqueous isopropanol is used, the reaction mixture used for alkalizing, etherification and crosslinking contains water introduced by the alkali hydroxide solution and, in some cases, additional quantities of water when crosslinking agent is added in the form of an aqueous solution. If the advantage residing in the use of isopropanol instead of water is to be fully utilized, care must be exercised that the entire quantity (by weight) of water introduced in the reaction mixture does not exceed the quantity (by weight) of isopropanol present; preferably, the quantity of water should not exceed two-thirds of the quantity of isopropanol. In this manner, cellulose ethers may be produced which are capable of adsorbing, for example, 60 times their own weight of water (WRV of 6000).

If water is used as the reaction medium, crosslinked cellulose ethers are obtained the water retention capacity of which is substantially below that, for example only half that, of cellulose ethers prepared under otherwise identical process conditions but in the presence of isopropanol, as described above. For many uses of the water retention capacity of these cellulose ethers this does not matter, and in some cases it even may be desirable. Cellulose ethers prepared and crosslinked in a purely aqueous reaction medium are, by the way, distinguished by the particular speed at which they adsorb water. Preferably, this manufacturing process is conducted using dry alkali cellulose, i.e. alkali cellulose prepared by spraying pulverized cellulose with concentrated, i.e. at least 20 per cent, aqueous alkali hydroxide solution in order to uniformly mix it with the required quantity of alkali, the resulting alkali cellulose being an almost dry powder. Alternatively, dip alkali cellulose may be used, i.e. alkali cellulose produced by immersing plates or ribbons of cellulose in an aqueous alkali hydroxide solution, followed by squeezing out and shredding. Alkali celluloses of this type are composed of a granular, nonagglomerating mixture. If a purely aqueous reaction medium is employed, the crosslinking process preferably is not deferred until after etherification. Advantageously, the crosslinking reaction is performed simultaneously with the etherification process. In a purely aqueous reaction medium, alkylene oxides, especially ethylene oxide, react very rapidly. Thus, discolored products may be obtained by accumulation of heat, but this is no disadvantage for some practical applications. Local overheating may be prevented by providing a uniform heat exchange. In mixed etherification processes, it is possible for the other etherification agent to assume the heat distributing role.

Similar to hitherto processes, the process of the present invention leads to crosslinked products which contain a certain water-soluble portion. For many purposes, this is no drawback, so that it is normally unnecessary to remove the water-soluble portion. In the following examples, the percentages by weight of the crosslinked cellulose ethers are stated which are soluble in water at 20° C.

The crosslinked cellulose ethers produced by the process of the invention may be used for various technical purposes, for example they may serve as absorbing materials in surgical and hygienic bandages, or as dehydrating agents, for example in aqueous emulsions.

The process of the present invention is distinguished in that sufficiently crosslinked products are obtained within a very short time, i.e. in about one hour, at relatively moderate reaction temperatures, preferably at temperatures up to about 80° C. Products with varying water retention values are obtained, depending upon the etherification and crosslinking conditions. Therefore, many different requirements can be met. The quantity of water retained may be extremely high and may amount, for example, to 60 times the weight of the crosslinked cellulose ether. The water adsorbed is so firmly attached to the crosslinked product that it cannot be removed therefrom, even if a centrifugal force is applied which corresponds to 2000 times the acceleration due to gravity. In the following examples, reference is made to the water retention value towards pure water at 20° C, determined after application of such a centrifugal force.

As a further advantage of the process of the invention, products are obtained which have a high water retention value relative to the quantity of crosslinking agent used. In this manner, products easily may be obtained which have a water retention capacity of 5 to 60 times their own weight. Further, the present process is very variable. This is due, in part, to the fact that, if a non-aqueous reaction medium is used, the efficiency of the crosslinking agent used according to the present invention is substantially independent of the quantity of reaction medium present, and, further, that the alkali resistance of the crosslinking agent is relatively high.

In the following examples, all percentages are by weight. Alkalization, etherification, and crosslinking are performed at the temperatures stated and while the reactants are thoroughly mixed. The abbreviation "MRV" means water retention value or capacity. It is stated in per cent by weight, calculated on the dry weight of the water-insoluble portion.

EXAMPLE 1

100 g of cellulose are alkalized in a reaction vessel, by intensive mixing over 45 minutes, with 51 g of aqueous sodium hydroxide solution (50%) in 300 g of 87% isopropyl alcohol at 20° C. 1.44 g of bis(acrylamido)-acetic acid are added and the mixture is crosslinked while further agitating for one hour at 50° C. Then 55 g of finely pulverized sodium monochloroacetate are added and the temperature is maintained at 70° C for one hour while continuously mixing the mass. During this time, etherification takes place. After the reaction product has cooled down, it is neutralized with acetic acid, washed with 80% methanol with suction, and dried at 50° C. The product thus obtained has a WRV of 2350 and contains 30.8 per cent of a water-soluble portion.

EXAMPLE 2

100 g of cellulose are alkalized in a reaction vessel with 91.5 g of an aqueous NaOH solution (28%) in 300 g of 87% isopropyl alcohol at 20° C by intensive mixing over 45 minutes. 65 g of finely pulverized sodium monochloroacetate and 1.44 g of bis(acrylamido)-acetic acid are added and etherification and crosslinking are simultaneously performed by continuing the mixing procedure for one hour at 80° C. After purification and drying as described in Example 1, a product is obtained which has a WRV of 1660 and contains 26.5 per cent of a water-soluble portion.

EXAMPLE 3

100 g of cellulose are alkalized in a reaction vessel with 91.5 g of an aqueous NaOH solution (28%) in 1,000 g of 87% isopropyl alcohol at 20° C, by intensive mixing for 45 minutes. 65 g of finely pulverized sodium monochloroacetate and 1.44 g of bis(acrylamido)-acetic acid are added and etherification and crosslinking are simultaneously performed by mixing for another hour at a temperature of 70° C. After purification and drying as described in Example 1, a product is obtained which has a WRV of 2645 and contains 28.8 per cent of a water-soluble portion.

EXAMPLE 4

100 g of cellulose are alkalized in a reaction vessel, by mixing thoroughly during 30 minutes, with 219 g of aqueous NaOH solution (13.7%) in 670 g of isopropyl alcohol (100%) at 20° C. 75 ml of ethylene oxide and 1.44 g of bis(acrylamido)-acetic acid are added and etherification and crosslinking are simultaneously performed by mixing for another hour at 70° C.

After purification as in Example 1 and drying at 60° C, a product is obtained which has a WRV of 3085 and contains 40.4 per cent of a water-soluble portion.

EXAMPLE 5

100 g of cellulose are sprayed in a reaction vessel with 91.5 g of an aqueous NaOH solution (28%) while constantly agitating and mixing is continued for 45 minutes at 20° C. Then a mixture of 65 g of finely ground sodium monochloroacetate and 0.22 g of bis(acrylamido)-acetic acid is added and etherification and crosslinking are simultaneously performed by continuing the mixing procedure for one hour at 80° C.

After washing to free from salts and drying as described in Example 1, a product is obtained which has a WRV of 3460 and contains 22.8 per cent of a water-soluble portion.

EXAMPLE 6

The procedure described in Example 5 is repeated, except that alkalization and etherification are performed in the presence of 300 g of 87% isopropyl alcohol.

After purification and drying, a product is obtained which has a WRV of 6045 and contains 25.2% of a water-soluble portion.

EXAMPLE 7

125 g of finely ground cellulose are sprayed in a reaction vessel with 228 g of aqueous NaOH solution (28%) and alkalized for 45 min. at 30° C while stirring.

Then a mixture of 169 g of sodium monochloroacetate and 1.56 g of bis(acrylamido)-acetic acid is added, and etherificaton and crosslinking are simultaneously performed by mixing for one hour at 80° C. After processing, the reaction product has a WRV of 18,300 and contains 62 per cent of a water-soluble portion.

It will be obvious to those skilled in the art that many modifications may be made within the scope of the present invention without departing from the spirit thereof, and the invention includes all such modifications.

What is claimed is:

1. In the process for the manufacture of water-adsorbing but at least partially water-insoluble cellulose ethers in which cellulose is alkalized in a liquid reaction medium and reacted with an etherification agent in a manner such that an at least preponderantly water-soluble celluose ether would be obtained in the case of a mere etherification process and in which, prior to, simultaneously with, or after the etherification prodcess, a reaction is effected with a crosslinking agent which is polyfunctional towards cellulose in an alkaline reaction medium, the improvement which comprises employing bis(acrylamido)-acetic acid as the crosslinking agent.

2. A process according to claim 1, in which etherification and crosslinking are effected in the presence of about 0.8 to 7.5 parts by weight of isopropanol, calculated on the weight of the cellulose.

3. A process according to claim 1, in which etherification and crosslinking are simultaneously effected, using a water-wet, alkalized cellulose, the water content of which is sufficiently low that it forms a loose, non-agglomerating powdery or granular mixture.

4. A process according to claim 1, in which the cellulose ether is crosslinked in a manner such that a cellulose ether results of which 50 per cent or more is insoluble in water.

* * * * *